(12) United States Patent
Su et al.

(10) Patent No.: US 10,182,731 B2
(45) Date of Patent: Jan. 22, 2019

(54) MEDICAL ELECTRODE AND LIMB CLAMP FOR AN ECG DEVICE

(71) Applicant: KONINKLIJKE PHILIPS N.V., Eindhoven (NL)

(72) Inventors: Jie Su, Shangyu (CN); Yuanchao Zhu, Kunshan (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 390 days.

(21) Appl. No.: 14/895,250

(22) PCT Filed: May 30, 2014

(86) PCT No.: PCT/IB2014/061829
§ 371 (c)(1),
(2) Date: Dec. 2, 2015

(87) PCT Pub. No.: WO2014/195835
PCT Pub. Date: Dec. 11, 2014

(65) Prior Publication Data
US 2016/0128600 A1 May 12, 2016

(30) Foreign Application Priority Data
Jun. 7, 2013 (WO) ............... PCT/CN2013/076906

(51) Int. Cl.
*A61B 5/0408* (2006.01)
*A61B 5/00* (2006.01)
(Continued)

(52) U.S. Cl.
CPC .......... *A61B 5/0408* (2013.01); *A61B 5/0424* (2013.01); *A61B 5/04026* (2013.01);
(Continued)

(58) Field of Classification Search
CPC .... A61B 5/0408; A61B 5/6884; A61B 5/6824
See application file for complete search history.

(56) References Cited

U.S. PATENT DOCUMENTS 2,815,749 A 12/1957 Friedman
3,067,749 A * 12/1962 Walters ............... A61B 5/0416
600/384
(Continued)

FOREIGN PATENT DOCUMENTS

CN 201312804 Y 9/2009
CN 201691920 U 1/2011
(Continued)

*Primary Examiner* — Lee S Cohen

(57) ABSTRACT

The present invention provides a medical electrode comprising a conductive metal base comprising a plate element and a boss formed on the plate element and a conductive support cylinder separate from the conductive metal base. The conductive support cylinder is rotatably mounted to the conductive metal base while remaining in electrical communication with said conductive metal base. The present invention also provides a limb clamp for an ECG device. According to the present invention, it is possible to prevent bending of the cable connecting with the medical electrode, thereby avoiding cable failure.

6 Claims, 6 Drawing Sheets

(51) Int. Cl.
  *A61B 5/0424* (2006.01)
  *A61N 1/04* (2006.01)
  *H01R 4/48* (2006.01)
  *H01R 4/56* (2006.01)
  *A61B 5/0402* (2006.01)
  *A61B 5/0428* (2006.01)

(52) U.S. Cl.
  CPC ........ *A61B 5/04286* (2013.01); *A61B 5/6824* (2013.01); *A61B 5/6828* (2013.01); *A61B 5/6838* (2013.01); *A61N 1/048* (2013.01); *H01R 4/48* (2013.01); *H01R 4/56* (2013.01); *A61B 2562/222* (2013.01); *A61B 2562/227* (2013.01); *A61N 1/0452* (2013.01); *A61N 1/0456* (2013.01); *A61N 1/0472* (2013.01); *H01R 2201/12* (2013.01)

(56) References Cited

U.S. PATENT DOCUMENTS

| | | | |
|---|---|---|---|
| 3,498,291 A * | 3/1970 | Bunn | A61B 5/0408 600/372 |
| 4,033,333 A * | 7/1977 | DeSalvo | A61B 5/04085 600/393 |
| 4,535,783 A | 8/1985 | Marangoni | |
| 4,612,936 A | 9/1986 | Yamaguchi et al. | |
| 4,781,197 A | 11/1988 | Fukuda | |
| 4,865,566 A * | 9/1989 | Rasmussen | A61B 5/0416 439/166 |
| 5,823,832 A | 10/1998 | Das | |
| 2003/0199940 A1 | 10/2003 | Nyberg | |
| 2009/0253975 A1 | 10/2009 | Tiegs et al. | |
| 2012/0071945 A1 | 3/2012 | Cejnar | |
| 2012/0130213 A1 | 5/2012 | Kusaka | |
| 2012/0272489 A1 | 11/2012 | Wang et al. | |
| 2016/0091920 A1 | 3/2016 | Belogolovy | |

FOREIGN PATENT DOCUMENTS

| | | |
|---|---|---|
| FR | 2657520 A1 | 8/1991 |
| GB | 2353417 A | 2/2001 |
| JP | 4831661 | 9/1973 |
| JP | 10179533 A | 7/1998 |
| RU | 2297211 | 4/2005 |

\* cited by examiner

MEDICAL ELECTRODE AND LIMB CLAMP FOR AN ECG DEVICE

CROSS-REFERENCE TO PRIOR APPLICATIONS

This application is the U.S. National Phase application under 35 U.S.C. § 371 of International Application No. PCT/IB2014/061829, filed on May 30, 2014, which claims the benefit of Chinese Patent Application No. PCT/CN2013/076906, filed on Jun. 7, 2013. These applications are hereby incorporated by reference herein.

FIELD OF THE INVENTION

The invention relates to an improved medical electrode, in particular to a medical electrode and a limb clamp for an ECG (electrocardiogram) device comprising such a medical electrode.

BACKGROUND OF THE INVENTION

An ECG device is widely used to obtain medical (i.e. biopotential) signals containing information indicative of electrical activity associated with the heart and pulmonary system. The signals obtained are one of the important bases for some disease diagnosis. The ECG device generally comprises a plurality (for example six) of torso electrodes which are applied to a torso portion of a patient and two pairs of limb electrodes which are mounted on a respective limp clamp and applied to the left and right limbs of the patient, respectively. These electrodes connect with an ECG module via the respective cables. In use, cable failure often occurs because of excessive bending cycles caused by various factors such as inappropriate placement of the electrodes, movement of the patient's body and/or their use model. Especially the cables connecting with the limb electrodes are easier subject to cable failure due to their unique use model.

FIG. 1 shows a conventional limb clamp 1 for an ECG device. The limb clamp 1 generally, comprises a first clamp portion 3, a second clamp portion 5, a spring element 7 interconnecting the first clamp portion 3 and the second clamp portion 5, and a medical electrode 9 mounted at the first clamp portion 3. The medical electrode 9 generally comprises a conductive support cylinder 11 that is fixed relative to the first clamp portion 3. When a cable 13 is inserted into and fixed to the support cylinder 11 of the medical electrode 9 that is fixed relative to the first clamp portion 3, the movement of the medical electrode 9 directly results in bending of the respective cable 1, thereby possibly causing cable failure. Further, it is possible for the left and right limb clamps to be applied reversely to the right and left limbs, which causes worse bending of the respective cables as shown in FIG. 1 and thus results in cable failure. Cable failure contributes to wrong or inaccurate signals, which in turn result in wrong or inaccurate diagnosis. Replacing a failed cable not only increases total cost of ownership for the ECG device but also is a waste of time and causes the ECG device to be out of service for a period of time. All in all, this issue has a big impact on the ECG industry all the time.

Past efforts focused primarily on increasing the durability of the cable itself, for example, thickening the lead wire of the cable, which further increases the cost of the ECG device and makes the patient feel uncomfortable.

Thus, there is a need to make improvements on the conventional medical electrode.

SUMMARY OF THE INVENTION

Accordingly, it is desirable to provide a medical electrode which may prevent the cable connecting with the medical electrode from flexing, thereby avoiding cable failure.

It is also desirable to provide a limb clamp for an ECG device which may prevent the cable connecting with an electrode of the limb clamp from flexing, thereby avoiding cable failure.

According to one aspect of the present invention, the present invention provides a medical electrode comprising:
 a conductive metal base comprising a plate element and a boss formed on the plate element; and
 a conductive support cylinder separate from the conductive metal base;
 wherein the conductive support cylinder is rotatably mounted to the conductive metal base while remaining in electrical communication with the conductive metal base.

Preferably, a recess is formed in one of the boss and a lower end of the conductive support cylinder, the other one of the boss and the lower end of the conductive support cylinder being rotatably mounted into the recess.

Preferably, a recess is formed in the boss and a lower end of the conductive support cylinder is rotatably mounted into the recess.

Preferably, a conductive bearing is disposed within the recess and the lower end of the conductive support cylinder is mounted into the conductive bearing.

Preferably, a plurality of conductive and elastic strips extending along the longitudinal axis of the conductive support cylinder and projecting radially outward are disposed on the circumferential surface of the lower end of the conductive support cylinder and the lower end of the conductive support cylinder is inserted snugly into the recess.

Preferably, the plurality of conductive and elastic strips are distributed evenly on the circumferential surface of the lower end of the conductive support cylinder.

Preferably, a spherical head is formed at the lower end of the conductive support cylinder, a corresponding spherical recess is formed in the boss, and the spherical head is received snugly in the spherical recess to form the universal joint knuckle.

Preferably, the conductive metal base comprises a first half portion and a second half portion.

Preferably, a flange is formed on an outer surface of the conductive support cylinder, a conductive spring is disposed between the flange and the boss, a nut having an inner flange is screwed to the boss to mount the conductive support cylinder to the conductive metal base.

Preferably, the medical electrode further comprises an electrolyte gel applied to the lower surface of the plate element.

Preferably, the conductive support cylinder comprises a through hole transverse to its longitudinal axis for receiving a cable.

Preferably, the conductive support cylinder further comprises a threaded hole formed along its longitudinal axis and communicating with the through hole.

According to the other aspect of the present invention, the invention provides a limb clamp for an ECG device comprising:
 a first clamp portion;
 a second clamp portion;
 a spring element interconnecting the first clamp portion and the second clamp portion; and
 an above-mentioned medical electrode mounted at the first clamp portion.

Preferably, an outer thread is formed on the outer surface of the boss, the boss passes through a through hole formed in the first clamp portion and a nut is screwed onto the outer thread so that the medical electrode is mounted onto the first clamp portion.

Preferably, the nut for mounting the medical electrode onto the first clamp portion and the nut for mounting the conductive support cylinder to the conductive metal base are the same nut.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PREFERRED EMBODIMENTS

The preferred embodiments of the present invention will be described in detail with reference to the drawings.

Figure 1:
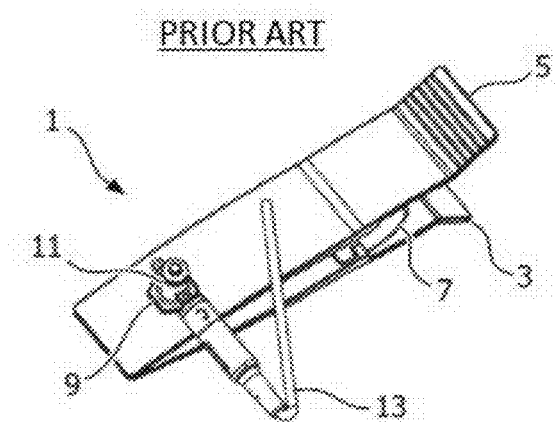
FIG. 1 is a perspective view of a conventional limb clamp for the ECG device showing a bend of a cable connecting with an electrode of the limb clamp.
Figure 2:
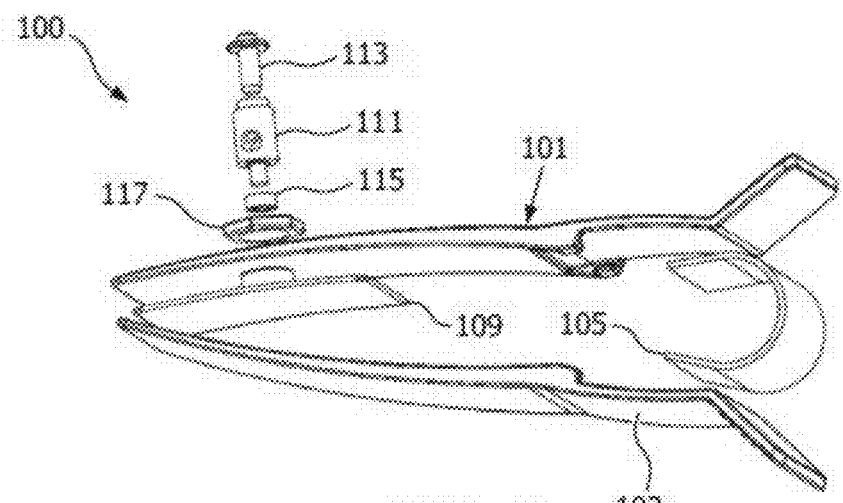
FIG. 2 is an exploded perspective view of a limb clamp for the ECG device with a medical electrode according to a first embodiment of the present invention.
Figure 3A:
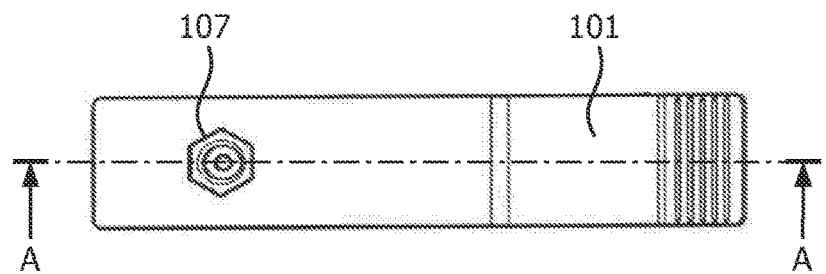
FIG. 3A is a top view of the limb clamp of FIG. 2 in an assembled state.
Figure 3B:
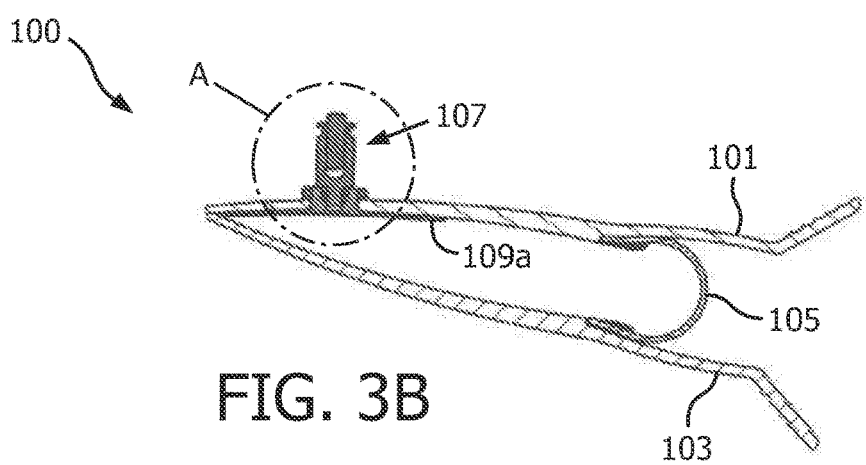
FIG. 3B is a cross sectional view taken along a line A-A of FIG. 3A.
Figure 3C:
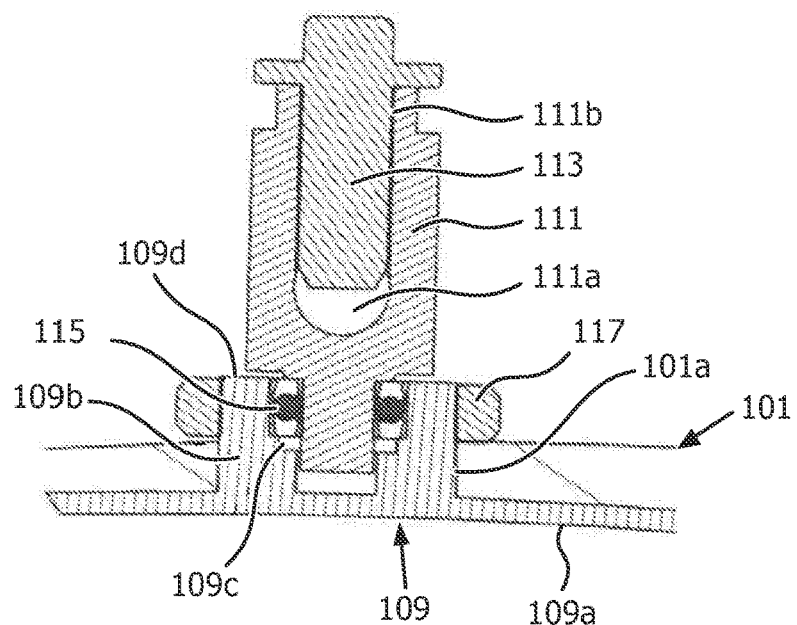
FIG. 3C is an enlarged view of an encircled portion A of FIG. 3B.

FIG. 2 is an exploded perspective view of a limb clamp for the ECG device with a medical electrode according to a first embodiment of the present invention. FIG. 3A is a top view of the limb clamp of FIG. 2 in an assembled state. FIG. 3B is a cross sectional view taken along a line A-A of FIG. 3A. FIG. 3C is an enlarged view of an encircled portion A of FIG. 3B. The limb clamp for the ECG device with a medical electrode according to a first embodiment of the present invention is generally designated by reference numeral 100. As shown in FIGS. 2, 3A, 3B and 3C, the limb clamp 100 for the ECG generally comprises a first clamp portion 101, a second clamp portion 103, a spring element 105 interconnecting the first clamp portion 101 and the second clamp portion 105, and a medical electrode 107 mounted at the first clamp portion 101. The structure and the connection of the first clamp portion 101, the second clamp portion 103 and the spring element 105 are known in the art.

The medical electrode 107 according to the first embodiment of the present invention generally comprises a conductive metal base 109 and a conductive support cylinder 111. The conductive metal base 109 comprises a plate element 109a and a boss 109b formed on the plate element 109a. In use, the lower surface of the plate element 109a contacts the body of a patient. Of course, an electrolyte gel may be applied to the lower surface of the plate element 109a. Although the boss 109b is shown to be formed integrally with the plate element 109a, the boss 109b may be formed separately from and attached to the plate element 109a in a known way, for example, by means of gluing, welding, or a thread connection. A recess 109c is formed in the boss 109b. Although the conductive support cylinder 111 is shown to be substantially cylindrical in shape, it may be in any suitable shape. The conductive support cylinder 111 may comprise a through hole 111a transverse to its longitudinal axis for receiving a cable. Preferably, the conductive support cylinder 111 further comprises a threaded hole 111b formed along its longitudinal axis and communicating with the through hole 111a. When a cable is inserted into the through hole 111a, a thumb screw 113 may be screwed into the threaded hole 111b to keep the cable in place in a reliable manner. Of course, it is also feasible that the conductive support cylinder 111 does not have the through hole 111a and the threaded hole 111b. In this case, the cable is attached to the conductive support cylinder 111 directly or by means of a sheath.

A bearing 115 made from a conductive material is disposed within the recess 109c formed in the boss 109b. The lower end of the conductive support cylinder 111 is mounted into the bearing 115 so that the conductive support cylinder 111 may rotate relative to the conductive metal base 109. Although the lower end of the conductive support cylinder 111 is shown to be thinner than the other portion of the conductive support cylinder 111, the lower end of the conductive support cylinder 111 may be as thick as or thicker than the other portion of the conductive support cylinder 111. In the shown embodiment, the bearing 115 is disposed within the recess 109c formed in the boss 109b. It should be understood that the bearing 115 alternatively may be disposed within a recess formed in the lower end of the conductive support cylinder 111. In this case, the upper end of the boss 109b is mounted into the bearing 115. The conductive bearing 115 allows the conductive support cylinder 111 to be rotatable relative to the boss 109b while keeping the conductive support cylinder 111 in electrical communication with the boss 109b.

An outer thread 109d is formed on an outer surface of the boss 109b. The boss 109b may pass through a through hole 101a formed in the first clamp portion 101 and then a nut 117 may be screwed onto the outer thread 109d of the boss 109b so that the medical electrode 107 is mounted onto the first clamp portion 101.

Figure 4A:
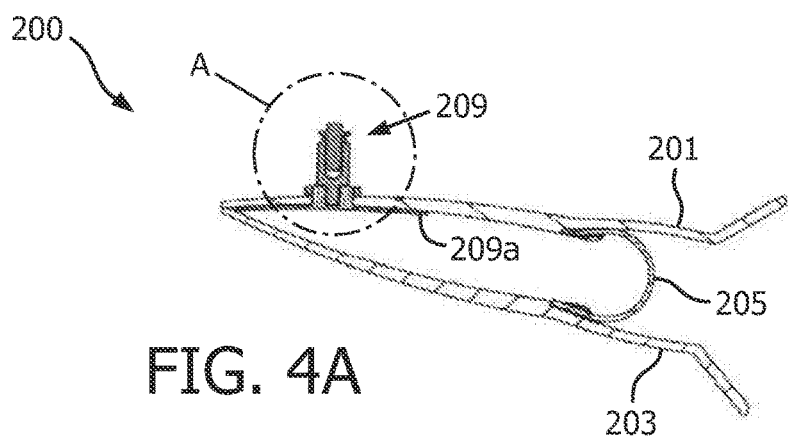
FIG. 4A is a cross sectional view similar to FIG. 3B, showing a limb clamp for the ECG device with a medical electrode according to a second embodiment of the present invention.
Figure 4B:
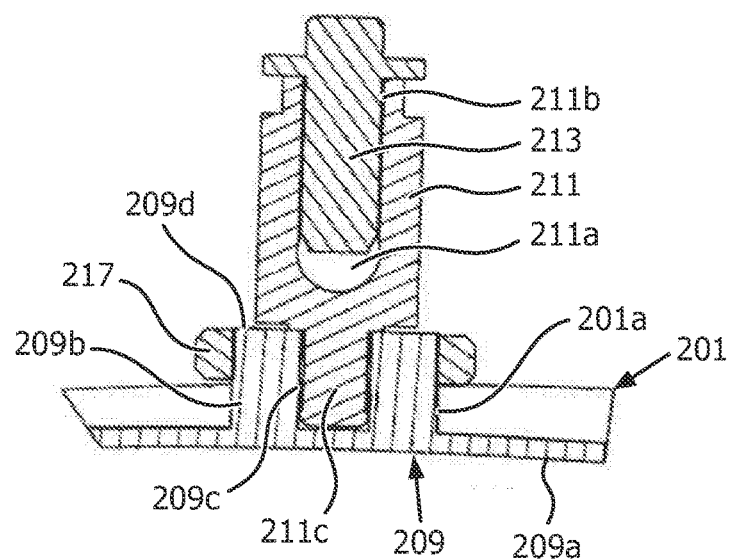
FIG. 4B is an enlarged view of an encircled portion A of FIG. 4A.
Figure 4C:
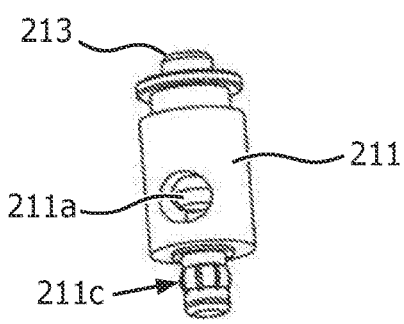
FIG. 4C is a perspective view of a support cylinder shown in FIG. 4B.

FIGS. 4A-4C illustrates a limb clamp for the ECG device with a medical electrode according to a second embodiment of the present invention. FIG. 4A is a cross sectional view similar to FIG. 3B. FIG. 4B is an enlarged view of an encircled portion A of FIG. 4A. FIG. 4C is a perspective view of a support cylinder shown in FIG. 4B. The limb clamp for the ECG device with a medical electrode according to a second embodiment of the present invention is generally designated by reference numeral 200. Parts of the limb clamp for the ECG device with the medical electrode according to the second embodiment corresponding to parts of the limb clamp for the ECG device with the medical electrode according to the first embodiment are indicated by the same reference numerals, plus "100". The description for the same parts is omitted for simplicity.

The limb clamp 200 for the ECG device with a medical electrode according to the second embodiment is substantially similar to the limb clamp 100 for the ECG device with the medical electrode according to the first embodiment, but does not include the bearing 115. In this embodiment, a plurality of conductive and elastic strips 211c extending along the longitudinal axis of the conductive support cylinder 211 and projecting radially outward are disposed on the circumferential surface of the lower end of the conductive support cylinder 211. The lower end of the conductive support cylinder 211 is inserted snugly into the recess 209c formed in the boss 209b. The elasticity of the elastic strips 211c allows the conductive support cylinder 211 to be rotatable relative to the boss 209b, while keeping the conductive support cylinder 211 in electrical communication with the boss 209b. Preferably, the plurality of conductive and elastic strips 211c is distributed evenly on the circumferential surface of the lower end of the conductive support cylinder 211. Further, the plurality of conductive and elastic strips 211c may be formed integrally with or separately from the conductive support cylinder 211. For example, a sleeve comprising the plurality of conductive and elastic strips 211c may be attached to the lower end of the conductive support cylinder 211.

Figure 5A:
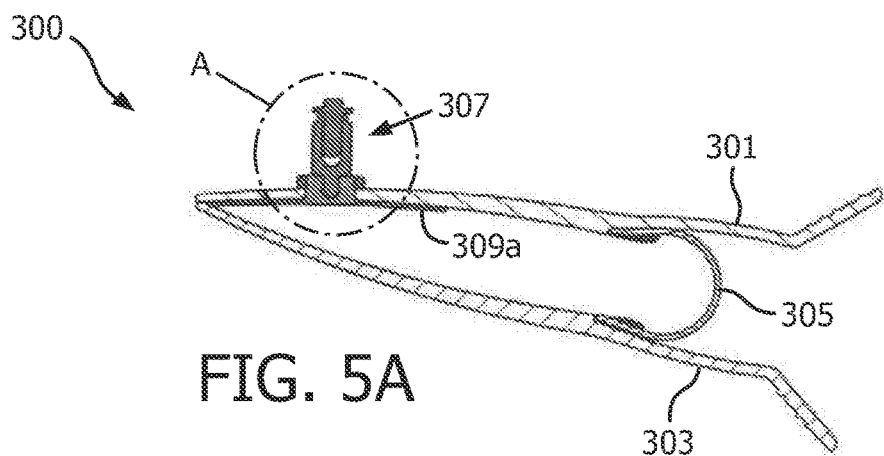
FIG. 5A is a cross sectional view similar to FIG. 3B, showing a limb clamp for the ECG device with a medical electrode according to a third embodiment of the present invention.
Figure 5B:
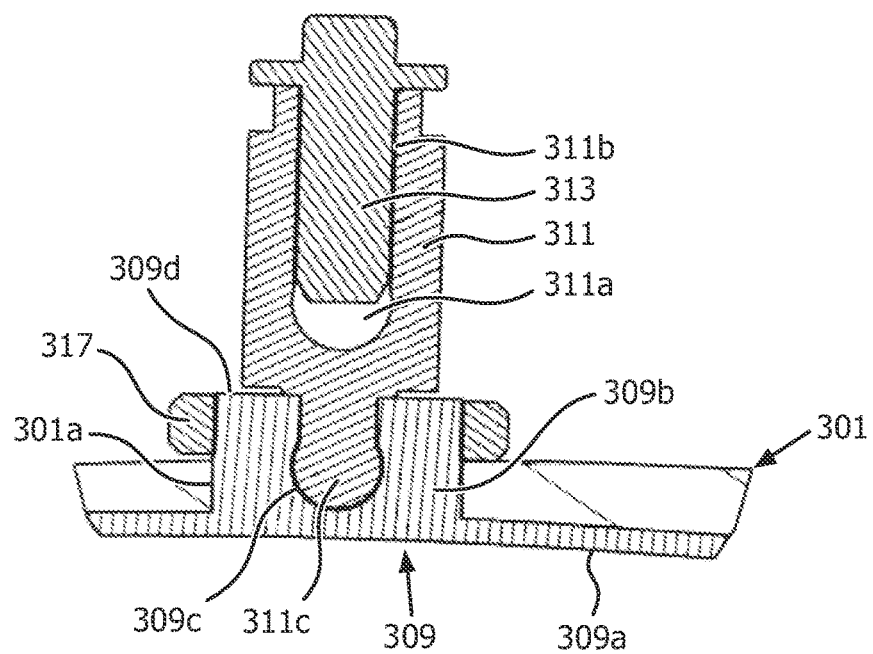
FIG. 5B is an enlarged view of an encircled portion A of FIG. 5A.
Figure 5C:
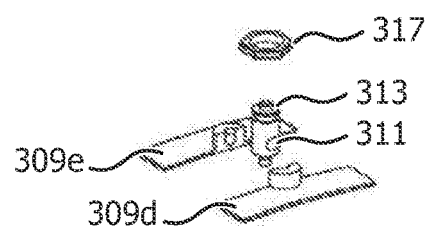
FIG. 5C is an exploded perspective view of a medical electrode shown in FIG. 5B.

FIGS. 5A-5C illustrate a limb clamp for the ECG device with a medical electrode according to a third embodiment of the present invention. FIG. 5A is a cross sectional view similar to FIG. 3B. FIG. 5B is an enlarged view of an encircled portion A of FIG. 5A. FIG. 5C is an exploded perspective view of a medical electrode shown in FIG. 5B. The limb clamp for the ECG device with a medical electrode according to a third embodiment of the present invention is generally designated by reference numeral 300. Parts of the limb clamp for the ECG device with the medical electrode according to the third embodiment corresponding to parts of the limb clamp for the ECG device with the medical electrode according to the first embodiment are indicated by the same reference numerals, plus "200". The description for the same parts is omitted for simplicity.

The limb clamp 300 for the ECG device with a medical electrode according to the third embodiment is substantially similar to the limb clamp 100 for the ECG device with the medical electrode according to the first embodiment, but does not include the bearing 115. In this embodiment, a universal joint knuckle is formed between the lower end of the conductive support cylinder 311 and the boss 309b. Specifically, a spherical head 311c is formed at the lower end of the conductive support cylinder 311 and a corresponding spherical recess 309c is formed in the boss 309b. The spherical head 311c is received snugly in the spherical recess 309c to form the universal joint knuckle. The universal joint knuckle allows the conductive support cylinder 311 to be rotatable relative to the boss 309b, while keeping the conductive support cylinder 311 in electrical communication with the boss 309b. To allow easy assembly of the medical electrode 307, the conductive metal base 309 may comprise a first half portion 309d and a second half portion 309e.

Figure 6A:
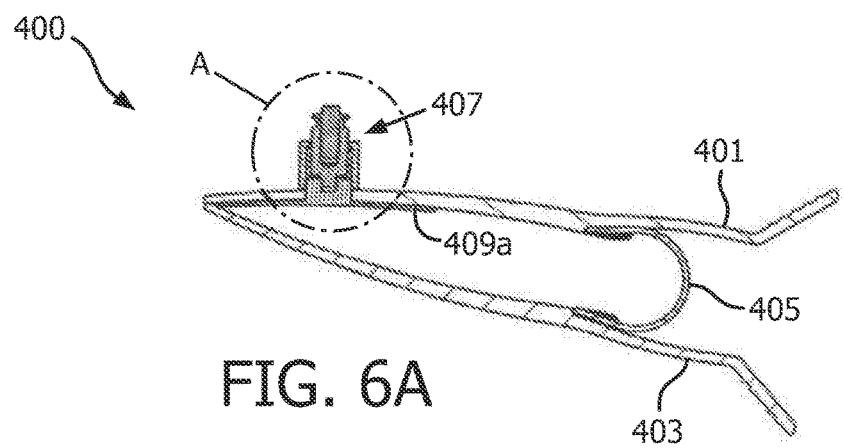
FIG. 6A is a cross sectional view similar to FIG. 3B, showing a limb clamp for the ECG device with a medical electrode according to a fourth embodiment of the present invention.
Figure 6B:
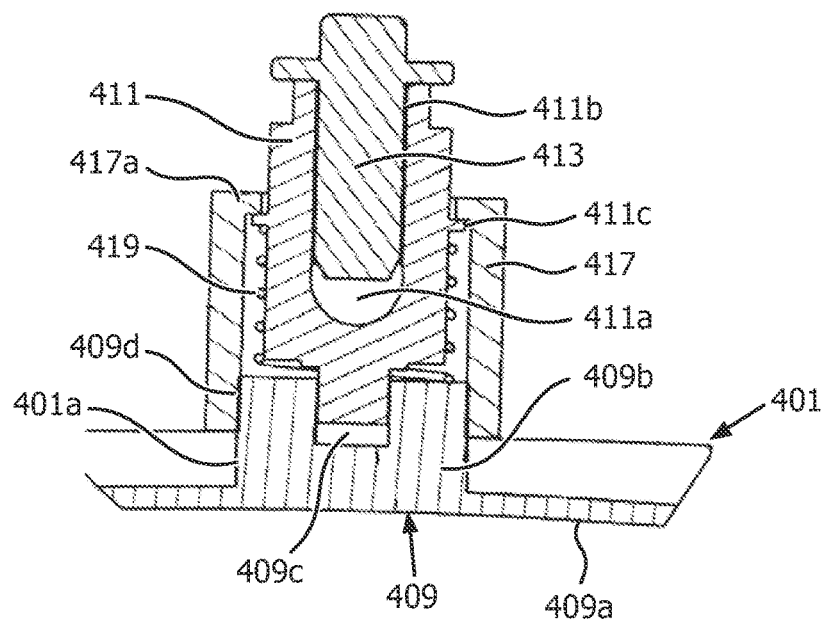
FIG. 6B is an enlarged view of an encircled portion A of FIG. 6A.
Figure 6C:
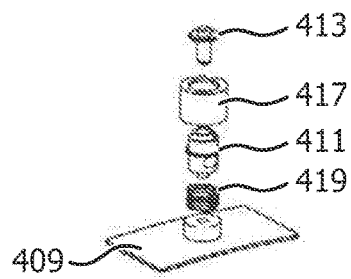
FIG. 6C is an exploded perspective view of a medical electrode shown in FIG. 6B.

FIGS. 6A-6C illustrate a limb clamp for the ECG device with a medical electrode according to a fourth embodiment of the present invention. FIG. 6A is a cross sectional view similar to FIG. 3B. FIG. 6B is an enlarged view of an encircled portion A of FIG. 6A. FIG. 6C is an exploded perspective view of a medical electrode shown in FIG. 6B. The limb clamp for the ECG device with a medical electrode according to a fourth embodiment of the present invention is generally designated by reference numeral 400. Parts of the limb clamp for the ECG device with the medical electrode according to the fourth embodiment corresponding to parts of the limb clamp for the ECG device with the medical electrode according to the first embodiment are indicated by the same reference numerals, plus "300". The description for the same parts is omitted for simplicity.

The limb clamp 400 for the ECG device with a medical electrode according to the fourth embodiment is substantially similar to the limb clamp 100 for the ECG device with the medical electrode according to the first embodiment, but does not include the bearing 115. In this embodiment, a flange 411c is formed on the outer surface of the conductive support cylinder 411. When the lower end of the conductive support cylinder 411 is inserted loosely into the recess 409c formed in the boss 409b, a conductive spring 419 is disposed between the flange 411c and the boss 409b. Further, the nut 417 having an inner flange 417a may be used to mount the conductive support cylinder 411 to the conductive metal base 409 and fix the metal electrode 407 to the first clamp portion 401. The conductive spring 419 allows the conductive support cylinder 411 to be rotatable relative to the boss 409b, while keeping the conductive support cylinder 411 in electrical communication with the boss 409b.

Figure 7:
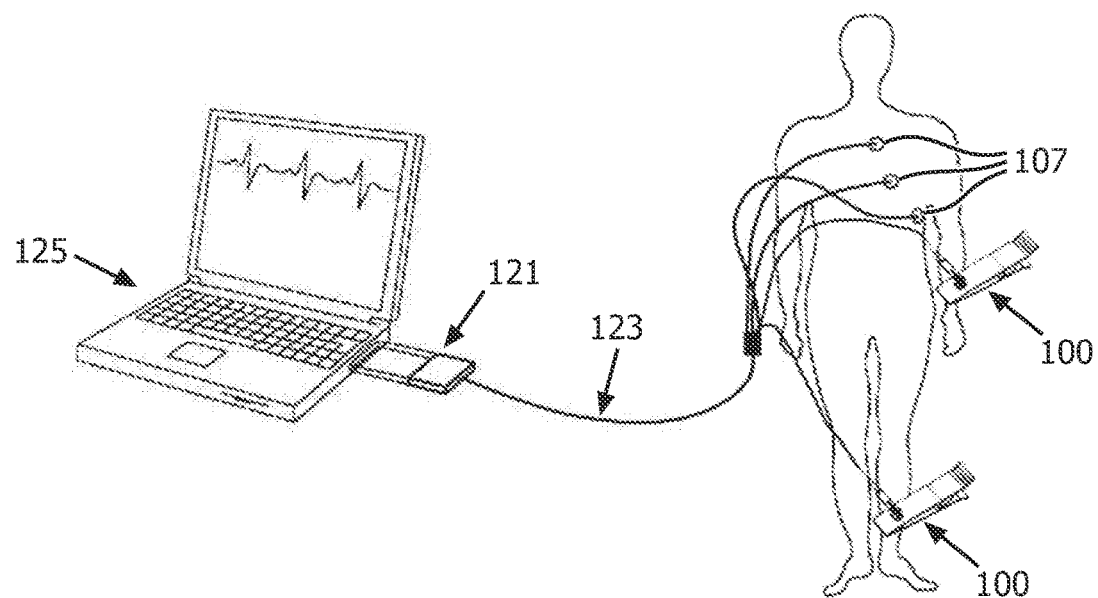
FIG. 7 is a schematic view showing that the medical electrodes and the limb clamps according to the present invention connect with an ECG module via the respective cables and are applied to the patient to record ECG signals.
Figure 8:
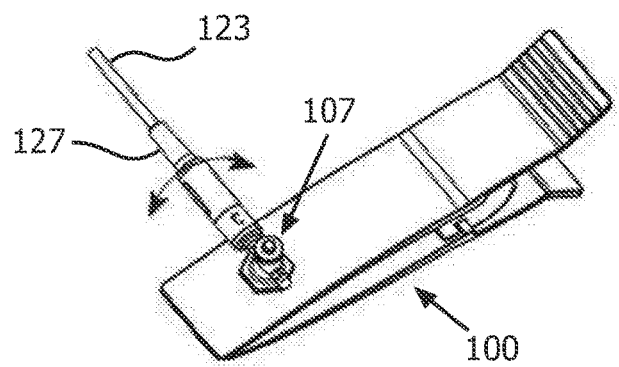
FIG. 8 is a perspective view of a limb clamp for the ECG device according to the present invention showing that there is no bending of the cable connecting with the electrode of the limb clamp.

FIG. 7 is a schematic view showing that the medical electrodes 107 and the limb clamps 100 according to the present invention connect with an ECG module 121 via the respective cables 123 and are applied to the patient to record ECG signals. The other pair of limb clamps 100 are not shown for simplicity. When the medical electrodes according to the present invention are applied to the patient's torso as torso electrodes, they are attached to the patient's torso by an adhesive plaster or a suction cup. The ECG module 121 connects with a computer 125 to show and analyze the recorded ECG signals. FIG. 8 is a perspective view of a limb clamp for the ECG device according to the present invention showing no bending of the cable connecting with the electrode of the limb clamp. A cable post 127 connecting with the cable 123 is inserted into the through hole 111a of the conductive support cylinder 111 of the medical electrode 107. Because the conductive support cylinder 111 of the medical electrode 107 may rotate relative to the conductive metal base 109 of the medical electrode 107, the cable 123 also rotates with the conductive support cylinder 111 as shown by a double-arrow line. Thus, no bending of the cable 123 connecting with the medical electrode 107 occurs irrespective of how the medical electrodes and the limb clamps move, thereby avoiding any cable failure.

In FIGS. 7 and 8, as an example, the medical electrodes and the limb clamps are the medical electrodes 107 and the limb clamps 100 according to the first embodiment of the present invention. Obviously, the medical electrodes and the limb clamps may be the medical electrodes and the limb clamps according to any one of the other embodiments of the present invention.

While the medical electrode according to the present invention is explained as a part of the ECG device in the embodiments, it should be understood that the medical electrode may be used with other medical instruments and may comprise additional components for other functions. Although the invention has been described in detail for the purpose of illustration based on what are currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

The invention claimed is:

1. A medical electrode comprising:
   a conductive metal base comprising a plate element and a boss formed on the plate element; and
   a conductive support cylinder separate from the conductive metal base;
   wherein the conductive support cylinder is mounted to the conductive metal base and is rotatable relative to the conductive metal base while remaining in electrical communication with the conductive metal base,
   wherein a recess is formed in one of the boss and a lower end of the conductive support cylinder; and
   a conductive bearing disposed within the recess,
   wherein the other one of the boss and the lower end of the conductive support cylinder is mounted into the conductive bearing and rotatable relative to the recess.

2. The medical electrode according to claim 1, further comprising an electrolyte gel applied to a lower surface of the plate element.

3. The medical electrode according to claim 1, wherein the conductive support cylinder comprises a through hole transverse to its longitudinal axis for receiving a cable.

4. The medical electrode according to claim 3, wherein the conductive support cylinder further comprises a threaded hole formed along its longitudinal axis and communicating with the through hole.

5. A limb clamp for an ECG device comprising:
   a first clamp portion;
   a second clamp portion;
   a spring element connecting the first clamp portion and the second clamp portion; and
   a medical electrode according to claim 1 mounted at the first clamp portion.

6. The limb clamp for an ECG device according to claim 5, wherein an outer thread is formed on the outer surface of the boss, the boss passes through a through hole formed in the first clamp portion and a nut is screwed onto the outer thread so that the medical electrode is mounted onto the first clamp portion.

* * * * *